United States Patent [19]

Kwok et al.

[11] Patent Number: 5,894,659

[45] Date of Patent: Apr. 20, 1999

[54] METHOD FOR INSPECTING LEAD FRAMES IN A TAPE LEAD BONDING SYSTEM

[75] Inventors: Tin Chu Samuel Kwok, Fanling; Hei Fat Isaac Ng, Shatin; Hoi-Man Yip; Ting-Chuen Pong, both of Kowloon; T. Roland Chin, Clear Water Bay, all of The Hong Kong Special Administrative Region of the People's Republic of China

[73] Assignee: Motorola, Inc., Schaumburg, Ill.

[21] Appl. No.: 08/616,980

[22] Filed: Mar. 18, 1996

[51] Int. Cl.⁶ .................................................. H01R 43/00
[52] U.S. Cl. ............................. 29/827; 29/833; 356/237; 356/394
[58] Field of Search ............................. 29/714, 720, 721, 29/705, 827, 833, 854; 356/394, 237; 358/101; 382/145

[56] References Cited

U.S. PATENT DOCUMENTS

| | | | |
|---|---|---|---|
| 4,851,902 | 7/1989 | Tezuka et al. | 358/101 |
| 5,406,699 | 4/1995 | Lyama | 29/827 |
| 5,549,716 | 8/1996 | Takahashi et al. | 29/827 X |
| 5,699,447 | 12/1997 | Alumot et al. | 382/145 |

*Primary Examiner*—Peter Vo
*Assistant Examiner*—Rick Kiltae Chang
*Attorney, Agent, or Firm*—George C. Chen

[57] ABSTRACT

In a tape lead bonding system, lead frames (3) are moved on a tape substrate (2) from a first station, where a first camera (12) takes an image of one half of one lead frame, to the next station, where a second camera (16) takes an image of the second half of the lead frame, while, at the same time, the first half of the next lead frame is being imaged by the first cameras(12). Both images of the particular lead frame (3) are then inspected by an inspection computer (15) before that lead frame reaches a bonding station so that bonding of a semiconductor die (21) to the lead frame (3) can be halted if a defect in the lead frame (3) is found. The system operates at the speed of the bonding unit (22), with out requiring the system to be slowed down to allow a full inspection of each lead frame (3) before the bonding step.

3 Claims, 5 Drawing Sheets

METHOD FOR INSPECTING LEAD FRAMES IN A TAPE LEAD BONDING SYSTEM

FIELD OF THE INVENTION

This invention relates to a method and apparatus for inspecting lead frames in a tape lead bonding system in which semiconductor dies are bonded to the lead frames, which are provided on a tape substrate.

BACKGROUND OF THE INVENTION

As is known, the lead frame is formed of a plurality of leads extending between an inner lead end for connection to the semiconductor die and an outer lead end for connection to a pin. The inner lead ends are relatively closely spaced together and arranged around the perimeter of a "window", in which the semiconductor die is to be bonded and the outer lead ends are relatively more separated than the inner lead ends so as to facilitate connecting the outer lead ends to individual pins of a semiconductor package.

Although the lead frame is mounted on a tape substrate for ease of handling on an automated manufacturing line, the lead frames are nevertheless somewhat fragile and can easily be damaged so as to have bent or broken leads or foreign matter inserted between the leads. Usually, the die and lead frame are tested after bonding and any such damaged devices can be rejected. But, if the rejection only occurs after the bonding step, then the whole device, including the die, is rejected, even if the fault lies in the lead frame.

Accordingly, it has been proposed to inspect the tips of the inner lead ends prior to bonding. An Inner Lead Bonder (ILB) manufactured by Shinkawa includes a visual inspection system for pre-bonding lead defect detection. The system can be programmed either to inspect all leads (100% inspection) or perform random checking at positions that are chosen manually. The followings steps are used to program the system to operate random checking:

1. Locate a first fiducial mark, i.e. the inner lead frame corner.
2. Locate a second fiducial mark, i.e. the inner lead frame corner at the other side. By using two fiducial marks, the system can handle both translation and rotation of the inner frame under inspection.
3. Learn the first lead group at the chosen region. The lead tip centers are computed at this stage.
4. Repeat step 3 until all required areas are covered.

For 100% inspection, the system will go via all the leads by using the above learning procedures. During operation, the two fiducial marks are first located so that the translation and rotation parameters can be obtained. Then a camera will move to each pre-programmed region using the offset parameters obtained previously. The leads at each inspection region will be found from each local window learned previously. If there is no lead found in the window, it prompts a broken lead defect. If all the leads are found in this region, it then computes the lead spacing between leads in order to detect lead bent defect.

However, this Shinkawa system uses a single camera to image the lead frame from above and inspects the lead frame part-by-part by moving the camera, thus requiring substantial time for a full inspection of each lead frame. Since the visual inspection process is embedded in the whole manufacturing process, utilising the vision system reduces the throughput of the bonding machine by about 40%. Although the Shinkawa system can inspect any part of the inner lead ends, it can only inspect a small region at a time and therefore requires several inspection steps to cover the entire inner lead ends. Furthermore, since the Shinkawa system is designed to inspect only the inner lead ends, defects such as foreign material inserted near the Polyimide Window are ignored. This results in undetected defects in lead frames, which are thus utilised in the die bonding process and incurs unnecessary waste of die.

BRIEF SUMMARY OF THE INVENTION

The present invention therefore seeks to provide an inspection apparatus for a tape lead bonding system which overcomes, or at least reduces the above-mentioned problems of the prior art.

Accordingly, the invention provides, in a first aspect, an inspection apparatus for a tape lead bonding system, the inspection apparatus including:

a tape guide for receiving and guiding a tape substrate having lead frames mounted at intervals therealong;

a first camera for imaging a first portion of a lead frame when the tape substrate is at a first position in the tape guide;

a second camera for imaging a second portion of the lead frame when the tape substrate is at a second position in the tape guide;

at least one lighting unit for lighting the tape substrate at the first and second positions from behind the tape substrate relative to the first and second cameras;

an inspection computer coupled to the first camera to receive a first image of the first portion of the lead frame and coupled to the second camera to receive a second image of the second portion of the lead frame, the inspection computer including an inspection unit for detecting the leads in the first and second images and for generating an alarm signal if it detects broken or bent leads or foreign matter bridging between leads.

In a second aspect, the invention provides an automatic tape lead bonding system including:

a source of tape substrate having lead frames mounted at intervals therealong, the lead frames incorporating leads;

at least one tape guide for receiving and guiding the tape substrate from the source to position adjacent lead frames at first and second stations;

a first camera at the first station for taking a first image of a first portion of a lead frame when the lead frame is at the first station;

a second camera at the second station for taking a second image of a second portion of the lead frame when the lead frame is at the second station;

an inspection computer coupled to the first camera to receive the first image and coupled to the second camera to receive the second image, the inspection computer including an inspection unit for detecting the leads in the first and second images and for generating an alarm signal if it detects broken or bent leads or foreign matter bridging between leads;

a bonding unit at a third station for receiving the lead frames on the tape substrate from the inspection apparatus and for automatically bonding semiconductor dies to the received lead frames, the bonding unit being controlled to stop operation if the inspection computer has generated the alarm signal.

In one embodiment, there is further provided at least one lighting unit for lighting the tape substrate at the first and second positions from behind the tape substrate relative to the first and second cameras.

Preferably, the first and second stations are separated such that when a lead frame is at the first station, a next adjacent lead frame is positioned at the second station.

In a preferred embodiment, the inspection unit includes a first device for overlaying scanlines perpendicular to the leads on each of the first and second images and a first detection device for detecting whether each of the leads extends over all the required scanlines and generating the alarm signal if not all the leads extend over all the required scanlines indicating that one or more leads are bent or broken. Preferably, the inspection unit further includes a second device for overlaying scanlines parallel to the leads on each of the first and second images and a second detection device for detecting whether any of the scanlines are broken and generating the alarm signal if one or more of the scanlines are broken indicating that one or more leads are bent or that foreign material is present.

Preferably, the inspection unit includes a controller, coupled to the first and second devices for controlling the second device only to operate if the first device has not generated the alarm signal.

According to a third aspect of the invention, there is provided a method of inspecting inner ends of leads of lead frames mounted on a tape substrate in a tape lead bonding system, the method including the steps of:

guiding a first lead frame on the tape substrate to a first station having a first camera thereat;

taking a first image of a first portion of the first lead frame using the first camera and transmitting the first image to an inspection computer;

guiding the first lead frame to a second station having a second camera thereat;

taking a second image of a second portion of the first lead frame using the second camera and transmitting the second image to the inspection computer;

inspecting the inner ends of the leads in the first and second images by the inspection computer and generating an alarm signal if broken or bent leads or foreign matter bridging between leads is detected;

guiding the first lead frame to a third station having a bonding unit thereat; and bonding a semiconductor die to the first lead frame if no alarm signal has been generated by the inspection computer.

Preferably, a second lead frame on the tape substrate is positioned at the first station when the first lead frame is at the second station.

In a preferred embodiment, the step of inspecting includes:

overlaying scanlines perpendicular to the inner ends of the leads on each of the first and second images;

detecting whether each of the leads extends over all the required scanlines and generating the alarm signal if not all the leads extend over all the required scanlines;

overlaying scanlines parallel to the leads on each of the first and second images; and detecting whether any of the scanlines are crossed by the leads or other matter and generating the alarm signal if one or more of the scanlines are crossed.

BRIEF DESCRIPTION OF THE DRAWINGS

One embodiment of the invention will now be more fully described, by way of example, with reference to the drawings, of which.

DETAILED DESCRIPTION OF THE DRAWINGS

Figure 1:
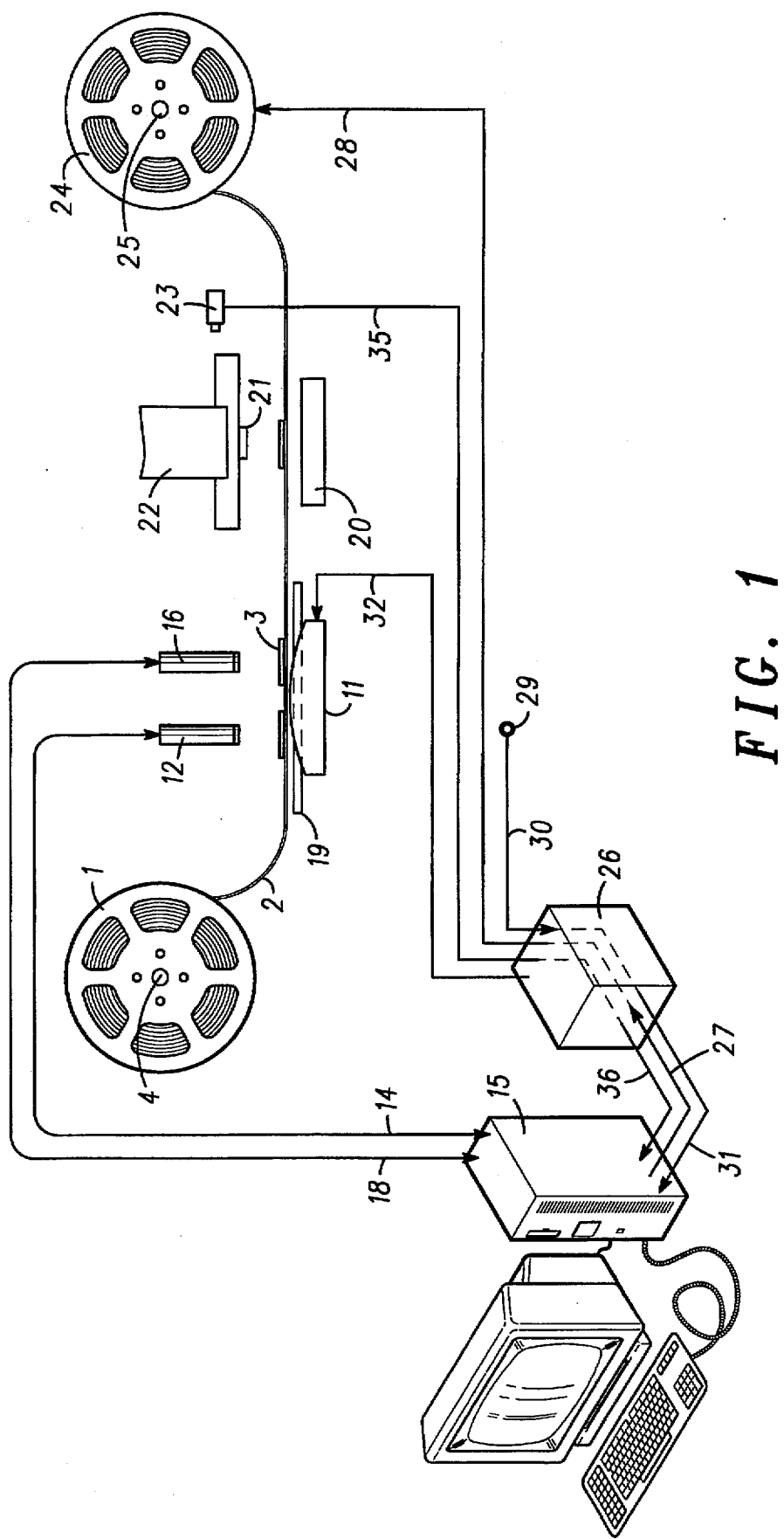
FIG. 1 shows a schematic block diagram of the automatic tape lead bonding system according to one embodiment of the invention.

Thus, as shown in FIG. 1, a supply reel 1 of tape substrate 2 having lead frames 3 mounted at intervals therealong is provided on a motorised spindle 4. As best shown in the upper part of FIG. 2, the tape substrate 2 can be of gelatin with sprocket holes 5 along both edges, similar to photographic film. The lead frames 3 are mounted on the tape substrate at appropriately spaced intervals such that when the tape substrate 2 is moved the lead frames are positioned at various stations along a manufacturing line, as will be described in more detail below.

Figure 2:
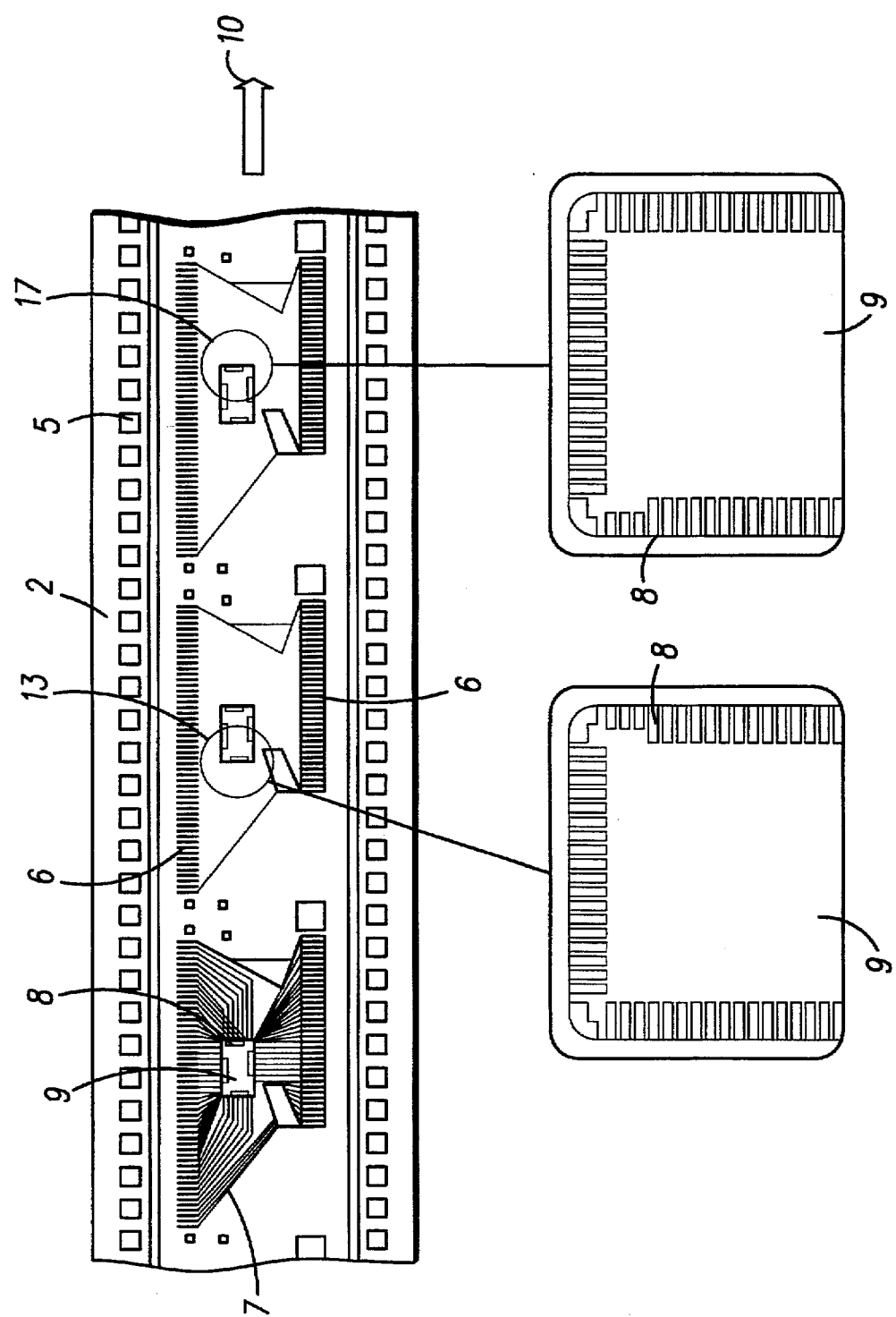
FIG. 2 shows three adjacent lead frames on a tape substrate as used in the system of FIG. 1, together with two images of two portions of the lead frames.

As is shown on the lead frame 3 at the left of FIG. 2, the lead frame includes outer lead ends forming pins 6 at the outer edges of the lead frame connected by middle portions 7 of the leads to inner lead ends 8 defining a polyimide window 9 on which a semiconductor die is to be bonded such that the connections of the die are coupled to the inner lead ends 8. For clarity, the middle portions 7 of the leads are not shown on the remaining lead frames 3 in FIG. 2.

As the tape substrate 2 is moved, in the direction of arrow 10 in FIG. 2, the tape substrate 2 reaches a tape guide 11, where it is received and guided along a track so that a lead frame 3 is accurately positioned at a first station. Movement of the tape substrate 2 is then stopped and a first camera 12 takes a detailed image of a left-hand portion of the polyimide window 9, as shown in FIG. 2, where the lower left-hand drawing of the inner lead ends 8 defining the polyimide window 9 is indicated by circle 13 as being the left side of the window 9. The image is transmitted via line 14 to the inspection computer 15. This can be an AISI 35EX vision computer manufactured by Applied Intelligent Systems, Inc. Such computers are widely used in industry for automatic inspection applications and operate in a manner well known to users of such computers.

Since the AISI 35EX vision computer's frame grabber can only handle image resolution with 512×512 pixels, it is not possible to capture the whole window in a single image while meeting the required measurement accuracy. The image takes in slightly more than half of the window 9. Thus, when the first image has been taken by the first camera 12, the tape substrate 2 is moved within the tape guide 11 until the lead frame 3 is accurately positioned at a second station. Movement of the tape substrate 2 is then stopped and a second camera 16 takes a detailed image of a right-hand portion of the polyimide window 9, as shown in FIG. 2, where the lower right-hand drawing of the inner lead ends 8 defining the polyimide window 9 is indicated by circle 17 as being the right side of the window 9. The image is transmitted via line 18 to the inspection computer 15.

In order to provide high-contrast and a reflection-free image for processing, a backlighting illumination technique is utilised. This involves positioning an electroluminescent (EL) lighting unit 19 in the tape guide 11 below the track on which the tape substrate 2 is guided so that the light from the unit 19 passes through the tape substrate 2, and, of course, the lead frame 3, to the cameras 12 and 16. The advantages of using an EL lighting unit are that it provides even lighting with little or no glare and that the units can be thin and flat, allowing it to fit into the tape guide. Such a configuration of two cameras and one tape guide and lighting unit reduces the space required for the apparatus in the lead bonding system to a minimum and avoids any major mechanical modification. However, it will be appreciated that more than one lighting unit, and more than one tape guide 11, can be utilised if the spacing of the cameras makes this appropriate.

After the two images are received by the inspection computer 15, they are processed to determined whether there are any defects in the inner lead ends 8 around the polyimide window 9. While this processing is taking place, the tape substrate 2 is moved on until the lead frame 3 reaches a bond guide 20 where it is accurately positioned at a third station. If no alarm signal has been generated by the inspection computer 15 to indicate a fault in the inner lead ends 8, a semiconductor die 21 is moved on a bond head 22 to the polyimide window 9 and is bonded to the lead frame 3, in a manner well known in the art. A bond head sensor 23 is used to sense when the bond head 22 is moved down towards the tape substrate 2 to bond the die 21 to the lead frame. The lead frame 3 having the semiconductor die 21 bonded thereto is then moved on the tape substrate onto a take-up reel 24 on a motorised spindle 25.

The system is controlled by an interface controller 26 connected to the inspection computer 15 and to various other elements of the system. The alarm signal generated by the inspection computer 15 when a fault is detected in the inner lead ends 8 is passed, via line 27, to the interface controller 26, which causes movement of the tape substrate 2 to stop. This stop signal is shown in FIG. 1 as passing via line 28 to reel 24, but it could alternatively or additionally be passed to reel 1. Once the faulty lead frame is removed an operator can issue a restart command from terminal 29 via line 30 to the controller 26, which restarts the inspection computer via line 31.

The interface controller 26 also controls the lighting unit 19, via line 32, although, of course, if desired, the lighting unit 19 can remain on at all times. The interface controller 26 also receives a signal from the bond head sensor via line 35 indicating that the bonding operation is complete and this information is passed on to the inspection computer via line 36.

Figure 3:
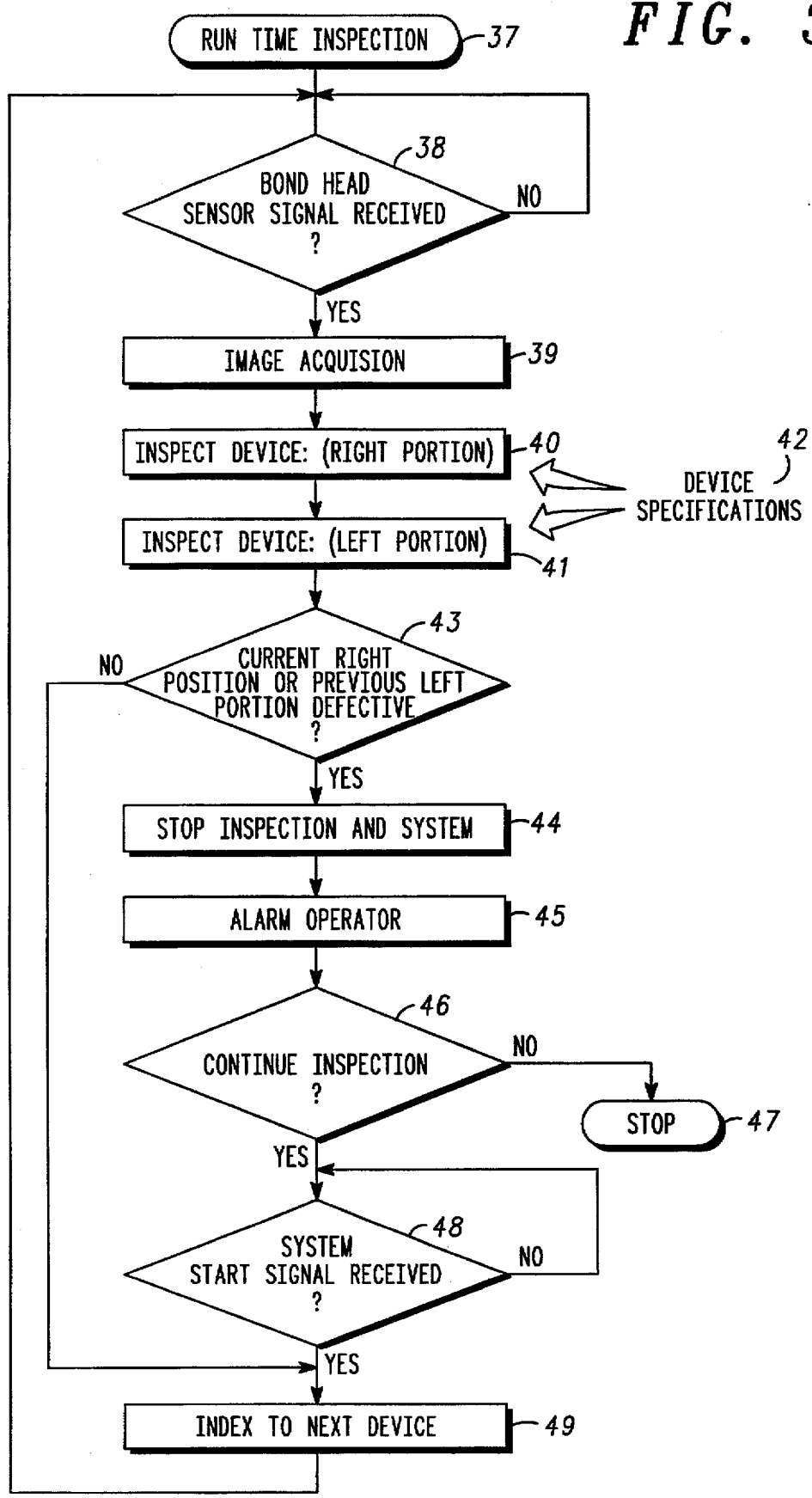
FIG. 3 is a flow diagram of the operation of the system of FIG. 1.

FIG. 3 shows a flow diagram for the inner lead end defect inspection system. Thus, when an inspection run is started, as indicated at step 37, advancement of the tape substrate 2 starts, and the system checks whether a signal is received from the bond head sensor 23, indicated at step 38. If no such signal is received, the flow returns to step 38. If there is a signal, indicating that the bond head 21 has moved down to bond a die to a lead frame at the third station, the first camera is activated to take an image of the first (left) portion of the inner lead ends 8, as indicated at step 39. At the same time, if a lead frame is in position at the second station, the second camera is activated to take an image of the second (right) portion of the inner lead ends 8, so that every time the tape substrate 2 is advanced so that a lead frame is moved from the first station to the second station, two images are captured, one by each camera and the image capturing instance, controlled by the vision computer 15 is synchronized by the bond head up-down movement sensed by the bond head sensor 23.

The two images received are then inspected for defects, as indicated at steps 40 and 41, utilising device specifications 42. Thus, the inspection computer performs the inspection once the image capturing process (about 70 msec.) is completed. Since images are received by the inspection computer from both the first and second cameras after an advancement of the tape substrate 2, it will be appreciated that the "right" image from the second camera corresponds to the lead frame of the previously received "left" image, not of the lead frame of the currently received "left" image. Therefore, the results of the inspections of the current "right" image and the previous "left" image are determined to see whether defects were found, as indicated at step 43.

If no defects were found, the tape substrate 2 is moved on to index to the next lead frame, as indicated at step 49, and the flow then returns to step 38. If, however, a defect was found, further inspection is stopped and the faulty lead frame is displayed on the monitor of the vision computer 15. At the same time, as indicated at step 44, the stop signal is generated and transmitted via line 28. An alarm signal is also generated to inform the operator that a fault has been found and that the system has been halted, as indicated at step 45. The operator then checks the displayed image for verification and can then decide, at step 46, to continue the inspection by issuing the restart signal via the terminal 29. Receipt of the restart signal is checked at step 48 and, if received, the flow moves on to index to the next lead frame at step 49, and then awaits receipt of the bond head sensor signal at step 38, as described above. If, on the other hand, the operator decides, at step, 46 to stop further inspection, the system stops, as at step 47.

Figure 4:
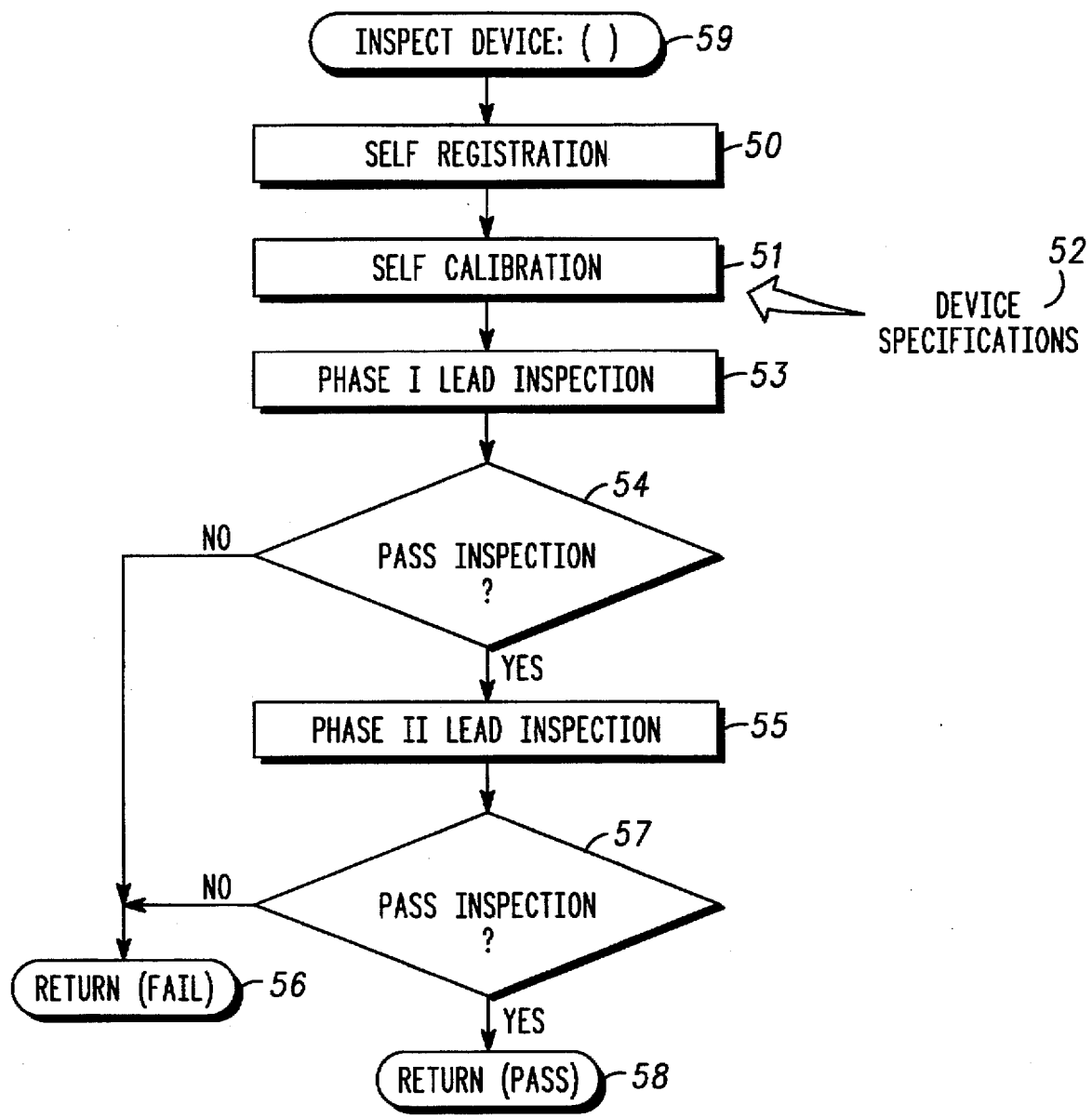
FIG. 4 is a flow diagram of the inspection procedure in the system of FIG. 1.

The inspection procedure is shown by the flow diagram of FIG. 4. As illustrated, initialisation of the inspection of a device, at step 59, is followed by a self-registration step 50 and a self-calibration step 51. The self-registration step 50 is used to accurately locate the polyimide window in the captured image. This step 50 involves thresholding the captured raw image, performing a morphological closing operation to remove the leads and obtain a closed region of the polyimide window, locating the left, top and right borders of the window, and determining two reference points, for example the projected corners of the window, by finding the intersected points of the three border lines. Once the two reference points have been located, the self-calibration step 51 determines the conversion factor for the image pixel to the real physical dimension using the known device specifications 52.

Figure 5:
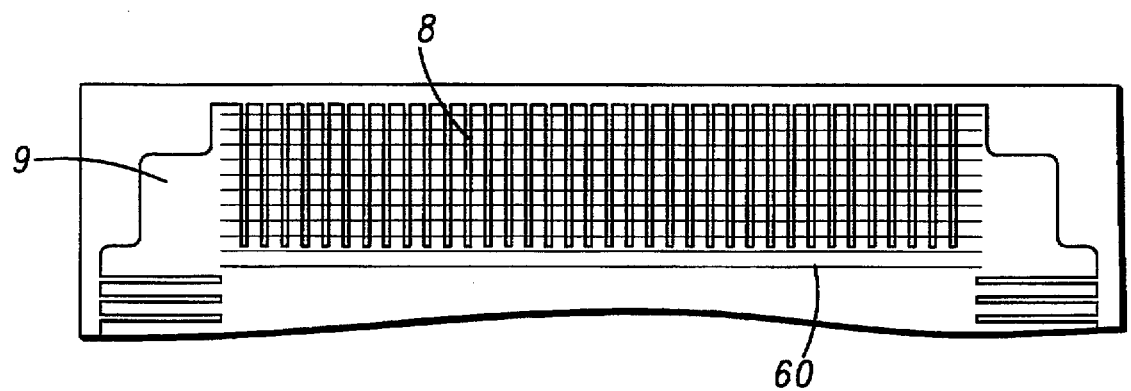
FIG. 5 shows the method of inspecting for bent or broken leads.

The first phase 53 of the lead inspection then follows. As shown in FIG. 5, the first phase 53 of the inspection involves generating scanlines 60 on the image perpendicular to the lead inner ends 8. Lead boundaries along the scanlines 60 are then inspected to make sure that the leads extend over all the required scanlines. If a lead boundary does not extend over a scanline that all the other leads extend over, it will be clear that the lead is either broken or bent. In such a case, the lead frame fails the first phase inspection. If the first phase of the inspection detects defects so that the first phase is not passed, then failure of the lead frame is reported, at step 56, and the second phase is not proceeded with. If, however, the lead frame image passes this phase of the inspection, as indicated at step 54, the second phase 55 of the inspection proceeds.

Figure 6:
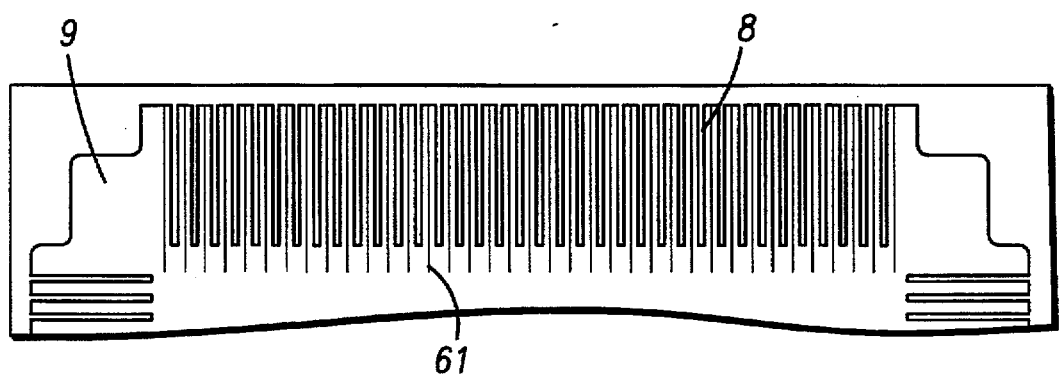
FIG. 6 shows the method of inspecting for bent leads or inserted foreign matter.

The second phase 55 of the inspection involves generating scanlines 61 on the image in the gaps between leads parallel to the lead inner ends 8, as shown in FIG. 6. The scanlines 61 are then inspected to make sure that the leads do not cross over any of the scanlines. If a scanline is "broken" by matter crossing over it, it will be clear that the lead is either bent or foreign matter is present. If the lead frame image passes this phase of the inspection, as indicated at step 57, passing of the lead frame is reported, as at step 58. If, however, the second phase of the inspection detects defects, then failure of the lead frame is reported at step 56. As mentioned above, the reporting of the failure or passing of the lead frame then causes the alarm signal to be generated or not.

Thus, it will be clear that the described system, in which the lead frames are moved on the tape substrate from one station to the next operates at the speed of the bonding unit, without requiring the system to be slowed down to allow a full inspection of each lead frame before the bonding step. Instead, an image of one half of one lead frame is made at a first station and then this is moved on to the next station, where an image of the second half of the lead frame is made, while, at the same time, the first half of the next lead frame is being imaged at the first station. Both images of a particular lead frame are then inspected before that lead frame reaches the bonding station so that bonding can be halted if a defect in the lead frame is found.

It will be appreciated that although only one particular embodiment of the invention has been described in detail, various modifications and improvements can be made by a person skilled in the art without departing from the scope of the present invention.

We claim:

1. A method of inspecting inner ends of leads of lead frames mounted on a tape substrate in a tape lead bonding system, the method including the steps of:

guiding a first lead frame on the tape substrate to a first station having a first camera thereat;

taking a first image of a first portion of the first lead frame using the first camera and transmitting the first image to an inspection computer;

guiding the first lead frame to a second station having a second camera thereat;

taking a second image of a second portion of the first lead frame using the second camera and transmitting the second image to the inspection computer;

inspecting the inner ends of the leads in the first and second images by the inspection computer and generating an alarm signal if a defect is detected guiding the first lead frame to a third station having a bonding unit thereat; and bonding a semiconductor die to the first lead frame if no alarm signal has been generated by the inspection computers, wherein the step of inspecting includes:

overlaying first scanlines perpendicular to the inner ends of the leads on each of the first and second images;

detecting whether each of the leads extends over all the first scanlines and Generating the alarm signal if not all the leads extend over all the first scanlines;

overlaying second scanlines parallel to the leads on each of the first and second images; and detecting whether any of the second scanlines are crossed and generating the alarm signal if one or more of the second scanlines are crossed.

2. A method of inspecting inner end of leads according to claim 1, wherein a second lead frame on the tape substrate is positioned at the first station when the first lead frame is at the second station.

3. A method of inspecting inner ends of leads of lead frames mounted on a tape substrate in a tape lead bonding system, the method including the steps of:

guiding a lead frame on the tape substrate to an inspection station having a camera thereat;

taking an image of the lead frame using the camera and transmitting the image to an inspection computer;

inspecting the inner ends of the leads in the image by the inspection computer and generating an alarm signal if a defect is detected;

guiding the lead frame to a bonding station having a bonding unit thereat; and bonding a semiconductor die to the lead frame if no alarm signal has been generated by the inspection computer, wherein the step of inspecting includes:

overlaying first scanlines perpendicular to the inner ends of the leads on the image;

detecting whether each of the leads extends over the first scanlines and generating the alarm signal if not all the leads extend over the first scanlines;

overlaying second scanlines parallel to the leads on the image; and detecting whether any of the second scanlines are crossed and generating the alarm signal if one or more of the second scanlines are crossed.

* * * * *